(12) United States Patent
Albrecht-Laatsch

(10) Patent No.: US 10,716,689 B2
(45) Date of Patent: Jul. 21, 2020

(54) METHOD FOR CONTROLLING AN ARTIFICIAL ORTHOTIC OR PROSTHETIC KNEE JOINT

(71) Applicant: OTTO BOCK HEALTHCARE GMBH, Duderstadt (DE)

(72) Inventor: Erik Albrecht-Laatsch, Rosdorf (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 0 days.

(21) Appl. No.: 14/380,055

(22) PCT Filed: Feb. 22, 2013

(86) PCT No.: PCT/EP2013/000519
§ 371 (c)(1),
(2) Date: Aug. 20, 2014

(87) PCT Pub. No.: WO2013/124071
PCT Pub. Date: Aug. 29, 2013

(65) Prior Publication Data
US 2015/0018972 A1 Jan. 15, 2015

(30) Foreign Application Priority Data
Feb. 22, 2012 (DE) .......................... 10 2012 003 369

(51) Int. Cl.
*A61F 2/72* (2006.01)
*A61F 2/64* (2006.01)
(Continued)

(52) U.S. Cl.
CPC .................. *A61F 2/72* (2013.01); *A61F 2/64* (2013.01); *A61F 2/68* (2013.01); *A61F 5/0123* (2013.01);
(Continued)

(58) Field of Classification Search
CPC ................ A61F 2/68; A61F 2002/6818; A61F 2002/7625; B25J 9/0006
See application file for complete search history.

(56) References Cited

U.S. PATENT DOCUMENTS

| 8,366,788 B2 * | 2/2013 | Moser ........................... 600/587 |
| 2003/0125814 A1 * | 7/2003 | Paasivaara ................ A61F 2/60 |
| | | 623/44 |

(Continued)

FOREIGN PATENT DOCUMENTS

| CN | 1711460 A | 12/2005 |
| DE | 102007053389 A1 | 5/2009 |

(Continued)

OTHER PUBLICATIONS

PCT International Search Report for PCT International Patent Application No. PCT/EP2013/000519, dated May 23, 2013.

*Primary Examiner* — Christie L Bahena
(74) *Attorney, Agent, or Firm* — Holland & Hart, LLP

(57) ABSTRACT

The invention relates to a method for controlling an artificial orthotic or prosthetic knee joint, on which a lower leg component is arranged and which is assigned a resistance device having at least one actuator, by means of which the bending resistance is modified depending on sensor data that is determined during use of the orthotic or prosthetic knee joint by means of a sensor, wherein the absolute angle of the lower leg component is determined exclusively by means of at least one inertial sensor, the angle determined is compared with at least one threshold value, and the bending resistance is modified when the threshold value is reached.

21 Claims, 3 Drawing Sheets

(51) Int. Cl.
*A61F 2/68* (2006.01)
*A61F 5/01* (2006.01)
*A61F 2/76* (2006.01)

(52) U.S. Cl.
CPC . *A61F 2002/6818* (2013.01); *A61F 2002/764* (2013.01); *A61F 2002/7625* (2013.01)

(56) References Cited

U.S. PATENT DOCUMENTS

| | | |
|---|---|---|
| 2004/0267379 A1 | 12/2004 | Pasolini |
| 2006/0249315 A1 | 11/2006 | Herr et al. |
| 2009/0076618 A1* | 3/2009 | Auberger ............ A61F 2/64 623/18.11 |
| 2009/0192619 A1* | 7/2009 | Martin ............... A61F 2/60 623/18.11 |
| 2010/0023133 A1* | 1/2010 | Fairbanks ........... A61F 2/64 623/24 |
| 2010/0174384 A1 | 7/2010 | Herr et al. |
| 2010/0305716 A1 | 12/2010 | Pusch et al. |
| 2012/0221120 A1 | 8/2012 | Seyr et al. |
| 2012/0226364 A1 | 9/2012 | Kampas et al. |
| 2012/0232674 A1 | 9/2012 | Kampas et al. |

FOREIGN PATENT DOCUMENTS

| | | |
|---|---|---|
| DE | 102008027639 A1 | 12/2009 |
| DE | 102009052887 A1 | 5/2011 |
| DE | 102009052895 A1 | 5/2011 |
| DE | 102009052894 A1 | 6/2011 |
| DE | 102009056466 A1 | 6/2011 |
| EP | 1237513 B1 | 10/2004 |
| WO | 01/43669 A1 | 6/2001 |
| WO | 2006069264 A1 | 6/2006 |
| WO | 2010129716 A1 | 11/2010 |
| WO | 2011057792 A1 | 5/2011 |

* cited by examiner

METHOD FOR CONTROLLING AN ARTIFICIAL ORTHOTIC OR PROSTHETIC KNEE JOINT

TECHNICAL FIELD

The invention relates to a method for controlling an artificial orthotic or prosthetic knee joint, on which a lower leg component is arranged and which is provided with a resistance device having at least one actuator, by means of which the bending resistance is modified as a function of sensor data which are determined by means of at least one sensor during use of the orthotic or prosthetic knee joint.

BACKGROUND

Prosthetic or orthotic knee joints replace or support the function of a natural knee joint. In order to achieve a maximum optimal functionality of the artificial knee joint, there are a multiplicity of designs on the market, which influence the behavior of the knee joints during the standing phase and the swing phase. Mechatronic knee joints are known, in which the movement situations are detected by means of a plurality of different sensors and, on the basis of the sensor data, a resistance device, by means of which the bending resistance (also referred to as flexion resistance) or the extension resistance is varied, is controlled. One basic problem is that the great variety of the possible movement situations can be encompassed only with difficulty in simple rules. In order to control actuators and brakes, therefore, so-called state machines are used, which are highly complex and represent many different activities. Disadvantages with this are the long development time and the use of elaborate components.

EP 1 237 513 B1 relates to a supporting device which replaces the existence or function of a limb and consists of at least two parts, connected to one another by an artificial joint, and a control device. The supporting device comprises a sensor, which detects an inclination angle relative to a line of gravity of a part connected to the joint and is coupled to the control device. The control device is arranged in such a way that it influences the joint on the basis of inclination angle data communicated by the sensor. In one configuration, the inclination angle sensor is arranged as a prosthetic knee joint on a thigh tube; in order to enhance the data situation, a second sensor may be arranged on the lower leg.

DE 10 2008 027 639 A1 relates to an orthotic joint for supporting an anatomical knee joint, having an upper joint part and a lower joint part which are connected to one another in an articulated fashion. A locking element for automatically unblocking and blocking the orthotic joint in an arbitrary position is provided, as is an actuation element for the locking element and a sensor means for detecting relevant information for the unblocking and blocking. An evaluation unit for evaluating the information acquired, and for forwarding this information to a control and/or regulating unit for the actuation element, is likewise provided. The sensor means comprises at least two sensors from the group: inclination sensors, rotation angle sensors, acceleration sensors or gyroscopes, for acquiring information describing the movement state and/or resting state of a person. Two sensors of one type or one sensor each of different types may be selected. All the sensors are arranged downward of the anatomical joint, in particular the knee joint.

SUMMARY

It is an object of the present invention to provide a method for controlling an artificial orthotic or prosthetic knee joint, with which a reliable and comfortable walking behavior of the prosthesis or orthesis can be achieved in a simple and economical way.

According to the method for controlling an artificial orthotic or prosthetic knee joint, on which a lower leg component is arranged and which is provided with a resistance device having at least one actuator, by means of which the bending resistance is modified as a function of sensor data which are determined by means of at least one sensor during use of the orthotic or prosthetic knee joint, the absolute angle of the lower leg component is determined exclusively by means of at least one inertial sensor, the angle determined is compared with at least one threshold value, and the bending resistance is modified, in particular reduced, when the threshold value is reached, in particular exceeded. In this way, sensor data which detects various measurement quantities, for example a torque, a force and an angle, which then need to be processed relatively elaborately, for a control algorithm to be obviated. The restriction to the use of absolute angles, which are measured by means of one or more inertial sensors, the absolute angle of the lower leg component being determined, is a simple and at the same time surprisingly reliable way in which control of a resistance change in a resistance or damping device of an artificial orthotic or prosthetic knee joint can be produced. In this case, furthermore, a plurality of threshold values are established, which trigger adaptation of the bending resistance when reached or exceeded or fallen below. In this way, it is possible to achieve a damping curve which is adapted to the patient and allows a smooth gait.

According to one refinement of the invention, an angular velocity of the lower leg component is calculated from the sensor data of the inertial sensors, and the bending resistance is reduced only when the angular velocity is not equal to zero. i.e., the lower leg component is moved in the extension or flexion (i.e., bending) direction. This ensures that a resistance change is carried out only during walking, as a function of the absolute angle of the lower leg component. The combination of an absolute angle with the angular velocity for the detection of a swing phase, and therefore establishment of the time when a bending resistance is reduced from standing phase damping to swing phase damping, has been found to be reliable even in the case of slow walking speeds. It is also possible to reliably determine other phases of the movement during walking by the combination of an absolute angle and angular velocity, so that the bending resistance or the extension resistance can be varied in a scope such that a smooth gait is obtained and the patient receives reliable and effective support.

According to one refinement of the invention, the absolute angle is determined exclusively by means of one or more inertial sensors, which is or are fastened on the lower leg component or on an orthotic or prosthetic component fastened distally thereon. The distally arranged orthotic or prosthetic components are, in particular, prosthetic feet or braces or arch supports for a natural foot in the case of an orthesis. The sensor or the sensors are preferably fastened medially and/or laterally on the respective lower leg component, in order to determine the absolute angle of the lower leg component, i.e., its position with respect to a fixed reference quantity, in particular the vertical.

The absolute angle may be determined by means of 2-dimensional (2D) or 3-dimensional (3D) magnetic field sensors, 2D or 3D acceleration sensors and/or 1-dimensional (1D), 2D or 3D gyroscopes. When a plurality of sensors are used, the sensor data of a plurality of inertial sensors may be merged together in order to be able to reliably establish the actual orientation of the lower leg component on the basis of a plurality of different sensor signals. Measurement inaccuracies or perturbations in the case of one sensor can then be compensated for by the other sensor or sensors.

The threshold value of the absolute angle of the lower leg component may be adjusted to the value which the lower leg component adopts at the end of the standing phase, so that particular physical properties of the patient can be taken into account by the individual adjustment. Likewise, a preferred movement pattern may be taken into account by adaptation of the threshold value of the absolute angle individually to the gait of the patient by the orthopedic technician responsible. The end of the standing phase is to be understood as meaning the instant within a walking cycle at which the front of the foot just still touches the ground during the rolling of the foot, immediately before the front of the foot loses contact with the ground and is lifted. The knee joint usually then bends further, so that flexion in the knee joint increases the distance of the foot from the ground.

The bending resistance may be switched between two fixed values so that there is a low bending resistance during the swing phase and a high bending resistance during the standing phase, or in an emergency mode. Such an emergency situation may be activated in the event of falling or stumbling. An increased bending resistance may then be provided in order to prevent unbraked knee flexion. The configuration of the actuator is advantageously selected in such a way that triggering by the actuator in order to reduce the damping cannot take place when there is an applied flexion moment. This may, for example, be achieved by dimensioning the power of the actuator to be less than the power which is necessary in order to overcome the counterpressure of a prosthetic joint loaded with a flexion moment. In this way, an actuation lock of the actuator is achieved by virtue of the technical power configuration or mechanical configuration, so that additional controls or sensors are not necessary. If the prosthesis user is in a position with a bent knee which is loaded, then, owing to the selected low power of the actuator, adjustment against the internal pressure of the system cannot take place, so that opening of the damping and spontaneous reduction of the damping can be avoided in potentially hazardous situations, even if the predetermined other parameters for varying the flexion damping are fulfilled.

According to one refinement of the invention, bending resistance is modified, in particular increased, when the angular velocity has reached a zero point and reversal of the movement direction of the lower leg component is determined. If the bending resistance is increased at the end of swing phase flexion, then increased security against unintended flexing in the event of collision with an obstacle is provided. If the patient stumbles, increasing the bending resistance makes it possible for the patient to be supported by the leg provided with the orthesis or prosthesis, without the knee joint flexing. If reversal of the movement direction is determined at the end of the swing phase, the bending resistance may be reduced in order to permit the initial standing phase flexion. Reversal of the movement direction at the end of the swing phase may be determined by the angular velocity reaching a zero point and the absolute angle being reduced.

The angular acceleration of the lower leg component may also be determined from the inertial sensor data, provision being made for the bending resistance to be increased, or not reduced, when a threshold value is exceeded. This is used in order to detect special situations, for example when stumbling. The angular acceleration is preferably determined when walking forward, so that the most frequent walking situations can be recorded and taken into account. Exceeding of a limit value by the angular acceleration can indicate that the smooth walking movement is interrupted, so that a damping value other than that of the swing phase damping seems expedient. In general, the flexion damping is then to be increased or left at a high value.

BRIEF DESCRIPTION OF THE DRAWINGS

An exemplary embodiment of the invention will be explained in more detail below with the aid of the figures, in which.

DETAILED DESCRIPTION

Figure 1:
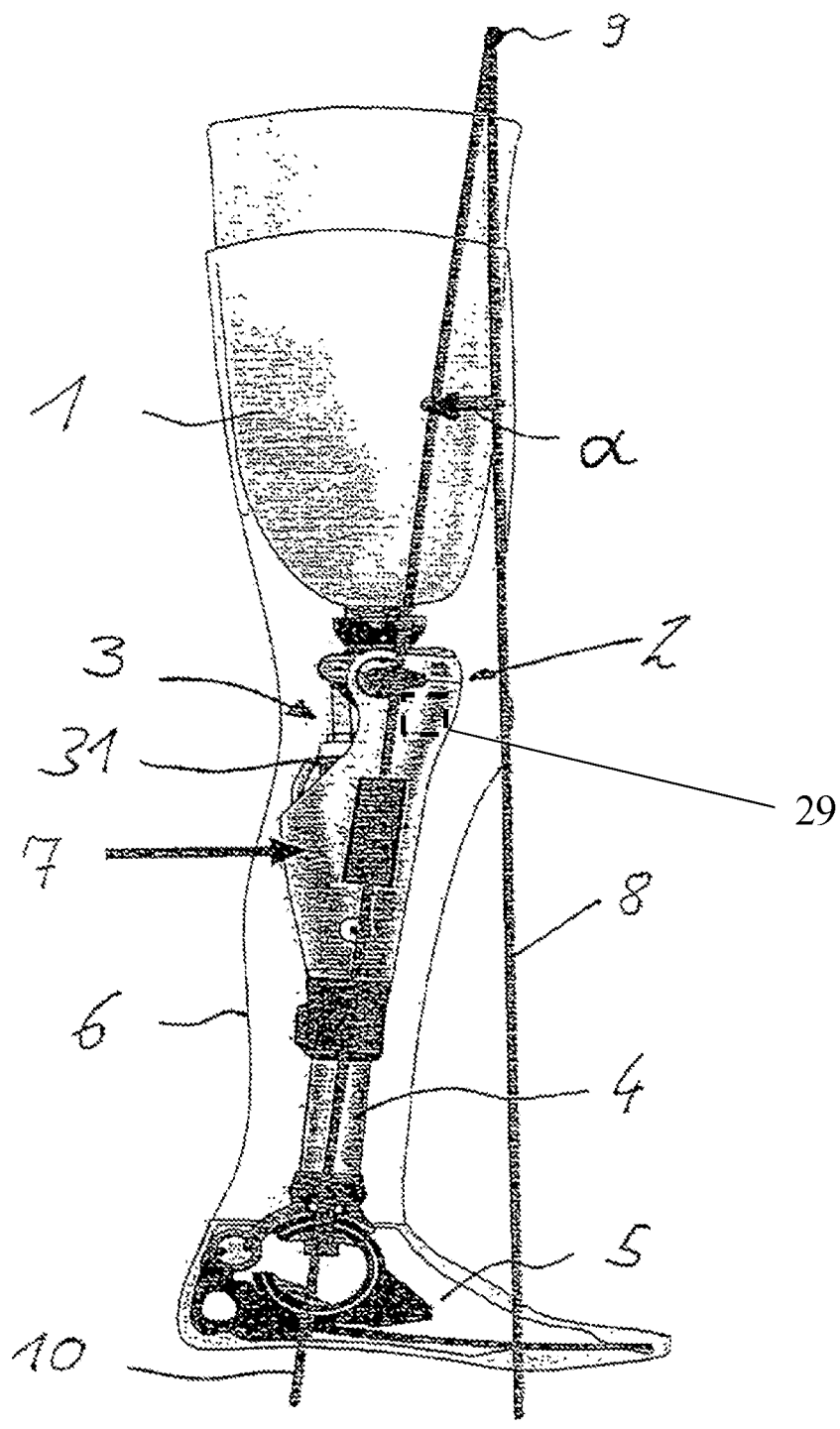
FIG. 1—shows a schematic representation of a prosthetic device.

FIG. 1 provides a schematic representation of a prosthetic leg with a prosthesis socket 1 for receiving an upper leg stump and for fixing the prosthetic leg to a patient. Arranged at the distal end of the prosthesis socket 1, there is a prosthetic knee joint 2 which is equipped with a resistance device 3, for example in the form of a hydraulic damper or a coil spring. At the distal end of the prosthetic knee joint 2, a lower leg tube 4 and a prosthetic foot 5 are provided as further distal components. The functional elements: prosthesis socket 1, prosthetic knee joint 2, lower leg tube 4 and prosthetic foot 5 are enclosed by a cosmetic covering 6 in order to impart a natural overall impression as much as possible.

In the exemplary embodiment represented, an inertial sensor 7 as an angle pickup is arranged on the lower leg component, which consists of the distal part of the prosthetic knee joint 2, the lower leg tube 4 and the prosthetic foot 5. The inertial sensor 7 may be formed as a magnetic field sensor, acceleration sensor or gyroscope. It is also possible for a plurality of inertial sensors 7 to be arranged on the lower leg component, for example in addition to the fitting at the distal part of the prosthetic knee joint 2 on the lower leg tube 4 or the prosthetic foot 5. The acceleration sensors and magnetic field sensors may be formed as 2D or 3D sensors, and in order to determine gyroscope data, a gyroscope may be formed as a 1 D, 2D or 3D gyroscope. A plurality of inertial sensors of the same type may be arranged on the lower leg component, likewise inertial sensors 7 of different types, for example an acceleration sensor and a gyroscope, may be fixed on the lower leg component.

The inertial sensor 7, which is formed as an angle sensor, determines the angle value of the lower leg component relative to a center of weight line 8, which extends through a center of gravity 9. The center of gravity 9 corresponds to the center of mass of the body of the patient, and the angle $\alpha$ is determined between the center of weight line 8 and the longitudinal extent of the lower leg component through the center of mass 9 of the body in the extended position of the prosthetic knee joint 2 at the end of the standing phase. The orientation of the lower leg component in FIG. 1 is defined by the connecting straight line 10 along the longitudinal extent of the lower leg tube 4 through the tilt axis of the prosthetic knee joint 2. In the position represented, the prosthetic knee joint 2 is in the extension position at the end of the standing phase. The existing angle $\alpha$ of the lower leg component relative to the center of weight line 8 is stored as a threshold value. At this value, there is extension of the prosthetic knee joint 2 and of the hip joint, and therefore a step rear position of the leg, and it is safe for the user to initiate the swinging phase. If a rolling process of the prosthetic foot 5 in the anterior direction is simultaneously detectable, which is manifested by an angular velocity $\alpha'>0$ and the angle increase, there is likewise a step in the anterior direction. On the basis of these data, an actuator 31 of the resistance device 3 of the prosthetic knee joint 2 is activated in such a way that existing standing phase damping is reduced and is kept low until the angular velocity $\alpha'$ has reached a zero point in the central swinging phase. An angle range for the position of the lower leg component at the end of the swing phase of a normal step may be stored on the basis of empirical values. If a full step is not executed, i.e., the angle range is not reached, or a non-smooth variation in the angular velocity $\alpha'$ is established, the resistance device 3 is influenced by means of the actuator 31 in such a way that there is an increased bending resistance. If the interrupted step is continued, a reduction of the flexion resistance may be carried out again in order to end the step.

Figure 2:
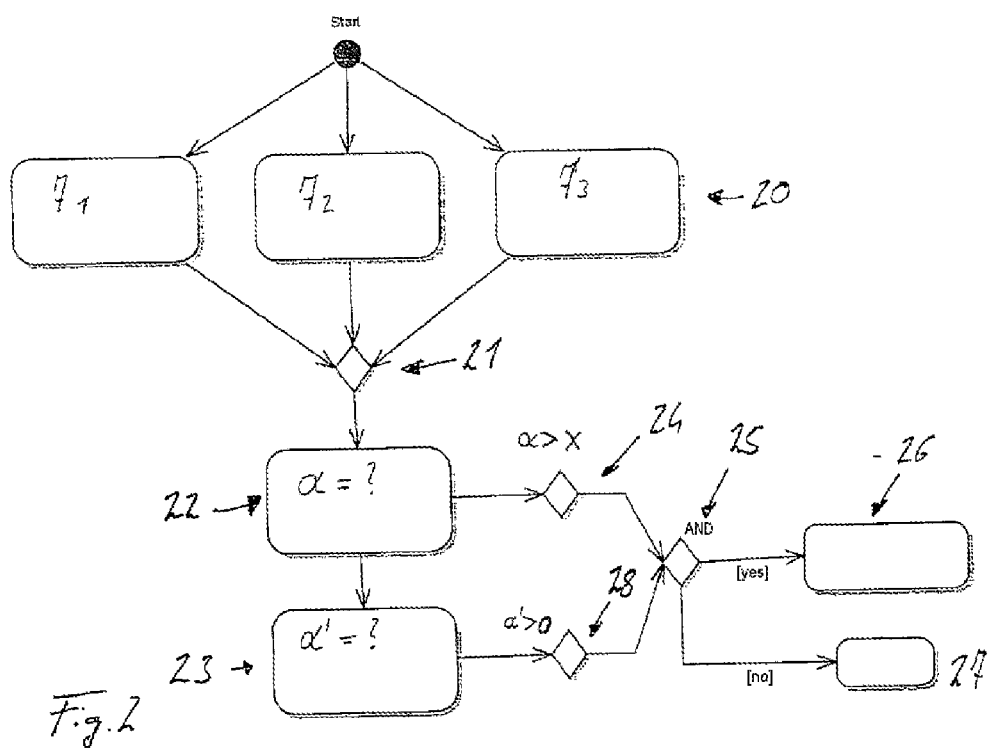
FIG. 2—shows a flow chart of the control.

FIG. 2 represents the functionality of the control as a diagram. After the start of the control, the respective sensor value is determined in a first step 20. A plurality of sensor values 71, 72, 73 may be measured by means of the inertial sensors 7. Besides the possibility of determining three sensor values 71, 72, 73 of the lower leg component, for example by using three different inertial angle sensors 7 such as a magnetic field sensor, an acceleration sensor and a gyroscope, it is also possible to determine a plurality of sensor values by using a plurality of inertial sensors 7 of the same type. In principle, it is also possible to detect the sensor value with only one inertial sensor 7.

The data detected by the inertial sensors 7 are merged in a further working step 21, in order to compensate for inaccuracies and have a data situation which is as complete as possible for the calculation of the absolute angle $\alpha$. If only one inertial sensor 7 is provided, the data does not need to be merged.

In a subsequent evaluation step 22, the sensor data 71, 72, 73 of the angles $\alpha$ of the lower leg component with respect to the weight line 8 are calculated. It is likewise possible to calculate the angular velocity $\alpha'$ of the lower leg component in parallel therewith in a further working step 23.

The angle $\alpha$, calculated for example by a Kalman filter, with respect to the weight line 8, is then compared in a further step 24 with a threshold value X which was established beforehand. As soon as the absolute angle $\alpha$ is greater than the preset threshold value X, in a control situation in which the angular velocity $\alpha'$ is not taken into account, the actuator 31 may be activated in a further step 26, in such a way that the damping device 3 adopts a reduced resistance for initiation of the swing phase. If the threshold value is not reached, in the alternative step 27 the actuator 31 is not correspondingly actuated and the resistance of the resistance device 3 remains unchanged.

If the angular velocity $\alpha'$ is also calculated together with the angle $\alpha$ in step 23, and the angular velocity $\alpha'$ is greater than zero, then a walking movement is detected in step 28. In a combining step 25, the angle $\alpha$ and the angular velocity $\alpha'$ are coupled with one another, and if both threshold values are present or are exceeded, the actuator is activated according to step 26, while if one of the two threshold values for the angle $\alpha$ or the angular velocity $\alpha'$ is absent, the actuator 31 is not activated according to step 27.

Figure 3:
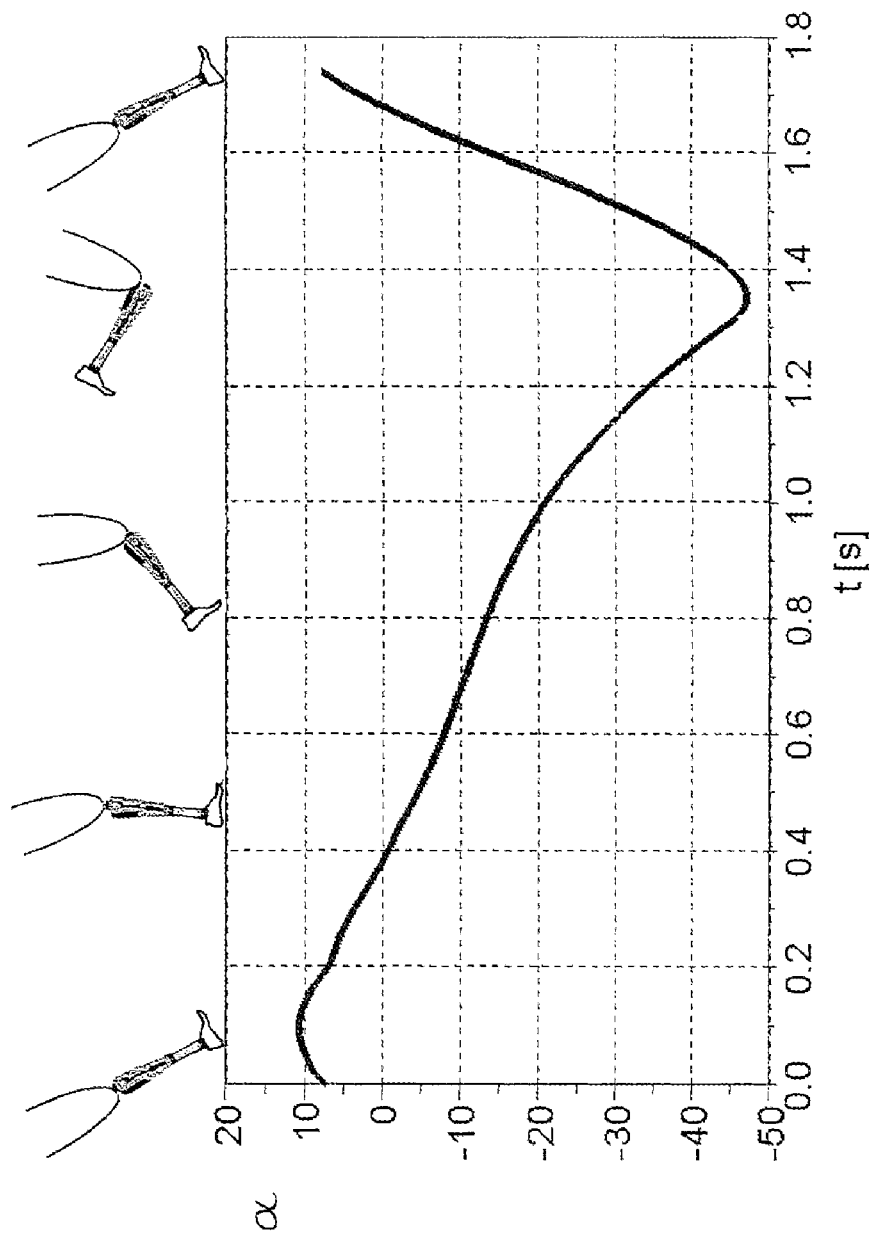
FIG. 3—shows a lower leg angle diagram.

FIG. 3 represents a diagram of the lower leg angle $\alpha$ as a function of time. The individual positions during a stepping cycle are represented above the diagram. The step begins with planting of the heel, the so-called heel strike, so that the lower leg angle $\alpha$ is initially slightly increased. In the course of continued stepping, the prosthetic foot is fully planted and after about 0.4 seconds, the lower leg, or the lower leg component, reaches the vertical, so that the lower limb angle $\alpha$ is 0°. As a result of movement further forward, the lower leg, or the lower leg component, is tilted further so that the lower leg a is increased in magnitude. The end of the standing phase is reached after about 0.8 seconds, and the front of the prosthetic foot leaves the ground so that swing phase flexion occurs. At the end of the swing phase, in the case of normal walking, the reversal point is reached at a lower leg angle of 45°. This is the case at about 1.3 seconds. A movement reversal subsequently takes place, the lower leg angle $\alpha$ is reduced in magnitude and approaches the vertical, until at about 1.7 seconds it reaches the vertical again and is then tilted further relative to the vertical, but this time in the positive angle range, by the foot being extended forward. Over the profile of the lower leg angle $\alpha$, a plurality of threshold values may be established for this lower leg angle $\alpha$. If these threshold values are reached or exceeded, or fallen below, depending on the direction in which the threshold value is considered, the variation of the bending resistance may be carried out; in particular, after a maximum bending angle is reached, the bending resistance may be increased in order to provide security against unintended and unbraked knee flexion joint in the event of stumbling. Simple and effective control of the damping of the resistance device can be carried out by means of the setting of the lower leg relative to the vertical.

It has been found that the simple algorithm described above can be used in order to switch to and fro between standing phase damping and swing phase damping. The control is particularly reliable when the angle value a is greater than a previously stored threshold value, which is adjusted by operating a control knob on the prosthetic device when the patient is in backward movement and the angular velocity $\alpha'$ is greater than zero. If both conditions are satisfied, the resistance device 3 may be switched over from high standing phase damping to lower swing phase flexion damping by switching a hydraulic valve or by releasing a lock of a brake device, for example.

The exclusive use of inertial sensors reduces the costs, since the torque sensors based on strain gauges for alternative methods are very expensive. Furthermore, inertial angle sensors are free from wear.

Besides the first derivative of the angle signal for determining the angular velocity, it is also possible to use the second derivative of the angle signal, in order to determine the angular acceleration. The acceleration signal may be used to detect falling, the angular acceleration exceeding a fixed limit value indicating that the smooth walking movement is interrupted and a different damping value would be more expedient, usually increasing the flexion resistance.

Furthermore, by observing the angle profiles, it is also possible to deduce the walking speed; in addition, not only can the resistance behavior, and therefore the damping behavior during the swing phase, be switched to and fro between two values in a binary fashion, but the switching may be adjusted in very small time intervals for discrete angle values or for any angle value, or any sampling of the angle value. For example, hydraulic valves may be adjusted stepwise or brake devices, which may likewise be used in resistance devices, may be adjusted in an adapted fashion in order to produce a smooth gait.

Furthermore, on the basis of the angle profiles, the resistance device may be adjusted in such a way as to allow standing phase flexion in the event of a heel strike with an extended joint, by reducing the flexion resistance. After this has happened, a progressive variation of the damping may also be provided, so that, after reduction of standing phase flexion after the heel strike, increasing damping occurs, which allows bending up to a particular angle value after the heel strike; in addition, a further increase in the angle is prevented by adjustment of the resistance device.

The artificial knee joints may be used both as prostheses, as described in the exemplary embodiment, and as ortheses. The resistance devices may be configured as simple locks, complex hydraulics or coil springs. By taking the angular velocity α into account, it is also possible to use drives in order additionally to permit flexion or extension. For security against undesired flexing or reduction of the damping under load, i.e., in the case of an applied flexion moment, the actuator may be configured in terms of power so that the switching power to be applied when a flexion moment occurs lies above the output power of the actuator, so that reduction of the damping and therefore abrupt flexing cannot occur.

P1. A method for controlling an artificial orthotic or prosthetic knee joint (2), on which a lower leg component (4, 5) is arranged and which is provided with a resistance device (3) having at least one actuator (31), by means of which the bending resistance is modified as a function of sensor data which are determined by means of a sensor (7) during use of the orthotic or prosthetic joint, characterized in that the absolute angle of the lower leg component (4, 5) is determined exclusively by means of at least one inertial sensor (7), the angle determined is compared with at least one threshold value, and the bending resistance is modified when the threshold value is reached.

P2. The method as described in paragraph P1, characterized in that an angular velocity of the lower leg component (4, 5) is calculated from the sensor data of the at least one inertial sensor (7), and the bending resistance is reduced only when the angular velocity is not equal to zero.

P3. The method as described in paragraph P1 or P2, characterized in that the absolute angle is determined exclusively by means of one or more inertial sensors (7), which is or are fastened on the lower leg component (4, 5) or on an orthotic or prosthetic component fastened distally thereon.

P4. The method as described in one of the preceding paragraphs P1-P3, characterized in that the absolute angle is determined by means of 2D or 3D magnetic field sensors, 2D or 3D acceleration sensors and/or 1D, 2D or 3D gyroscopes.

P5. The method as described in one of the preceding paragraphs P1-P4, characterized in that the sensor data of a plurality of inertial sensors (7) are merged together.

P6. The method as described in one of the preceding paragraphs P1-P5, characterized in that the threshold value of the absolute angle of the lower leg component (4, 5) is adjusted to the value which the lower leg component (4, 5) adopts at the end of the standing phase.

P7. The method as described in one of the preceding paragraphs P1-P6, characterized in that the bending resistance is switched between two fixed values.

P8. The method as described in one of the preceding paragraphs P1-P7, characterized in that the bending resistance is modified when the angular velocity has reached a zero point and reversal of the movement direction of the lower leg component (4, 5) is determined.

P9. The method as described in one of the preceding paragraphs P1-P8, characterized in that the angular acceleration of the lower leg component (4, 5) is determined, and the bending resistance is increased, or not reduced, when a threshold value is exceeded.

The invention claimed is:

1. A method for controlling an artificial orthotic or prosthetic knee joint of an orthosis or prosthesis, the orthosis or prosthesis including a lower leg component arranged distal of the knee joint, the method comprising:
   providing at least one inertial sensor and a resistance device, the at least one inertial sensor being positioned on the lower leg component, and the resistance device having at least one actuator;
   determining that an absolute angle of the lower leg component has reached a threshold value using a control device and sensor data provided to the control device during a gait cycle by only the at least one inertial sensor;
   determining an angular velocity of the lower leg component using a control device and sensor data provided to the control device during the gait cycle by the at least one inertial sensor;
   modifying a bending resistance of the orthotic or prosthetic knee joint with the resistance device during the gait cycle based on the absolute angle reaching the threshold value and the angular velocity; and
   adjusting the threshold value of the absolute angle of the lower leg component to a value of the absolute angle of the lower leg component at an end of a standing phase of a patient.

2. A method for controlling an artificial orthotic or prosthetic device, the artificial orthotic or prosthetic device comprising:
   a knee joint;
   a lower leg component coupled to the knee joint, the lower leg component being positioned distal to the knee joint;
   a resistance device including an actuator, the resistance device being configured to modify a bending resistance of the knee joint;
   one or more inertial sensors configured to measure an absolute angle of the lower leg component; and
   a control device in electronic communication with the one or more inertial sensors;
   the method comprising:
   determining that the absolute angle of the lower leg component has reached a threshold value using the control device and information provided to the control device during a gait cycle by only the one or more inertial sensors; and
   modifying the bending resistance of the knee joint using the resistance device based upon the absolute angle of the lower leg component reaching the threshold value.

3. The method of claim 2 comprising:
   determining that an angular velocity of the lower leg component is not zero using the control device and information provided to the control device during the gait cycle by the one or more inertial sensors; and
   reducing the bending resistance of the knee joint based upon the angular velocity of the lower leg component not being zero.

4. The method of claim 2 comprising determining that the absolute angle of the lower leg component has reached the threshold value using the control device and information provided to the control device during the gait cycle by only the one or more inertial sensors positioned distal to the knee joint.

5. The method of claim 2 wherein the one or more inertial sensors include at least one of a two dimensional magnetic field sensor, a three dimensional magnetic field sensor, a two dimensional acceleration sensor, a three dimensional acceleration sensor, a one dimensional gyroscope, a two dimensional gyroscope, and a three dimensional gyroscope.

6. The method of claim 2 comprising determining that the absolute angle of the lower leg component has reached the threshold value using the control device and information provided to the control device during the gait cycle by at least two of the inertial sensors.

7. The method of claim 2 comprising adjusting the threshold value to a value of the absolute angle of the lower leg component at an end of a standing phase of a patient.

8. The method of claim 2 wherein modifying the bending resistance of the knee joint using the resistance device based upon the absolute angle of the lower leg component reaching the threshold value includes switching the bending resistance to one of two fixed values.

9. The method of claim 2 comprising:
determining, using the control device and information provided to the control device during the gait cycle by the one or more inertial sensors, that an angular velocity of the lower leg component has reached zero signifying a reversal of a movement direction of the lower leg component; and
modifying the bending resistance of the knee joint using the resistance device based upon the angular velocity of the lower leg component reaching zero signifying the reversal of the movement direction of the lower leg component.

10. The method of claim 2 comprising:
determining that an angular acceleration of the lower leg component has exceeded a threshold acceleration value using the control device and information provided to the control device during the gait cycle by the one or more inertial sensors; and
maintaining or increasing the bending resistance of the knee joint based upon the angular acceleration of the lower leg component exceeding the threshold acceleration value.

11. The method of claim 2 comprising determining that the absolute angle of the lower leg component has reached the threshold value using the control device and electronic signals provided to the control device during the gait cycle by only the one or more inertial sensors.

12. An artificial orthotic or prosthetic device comprising:
a knee joint;
a lower leg component coupled to the knee joint, the lower leg component being positioned distal to the knee joint;
a resistance device including an actuator, the resistance device being configured to modify a bending resistance of the knee joint;
one or more inertial sensors configured to measure an absolute angle of the lower leg component; and
a control device in electronic communication with the one or more inertial sensors;
wherein the control device is configured to determine that the absolute angle of the lower leg component has reached a threshold value using information provided to the control device during a gait cycle by only the one or more inertial sensors; and
wherein the control device is configured to modify the bending resistance of the knee joint using the resistance device based upon the absolute angle of the lower leg component reaching the threshold value.

13. The artificial orthotic or prosthetic device of claim 12
wherein the control device is configured to determine that an angular velocity of the lower leg component is not zero using information provided to the control device during the gait cycle by the one or more inertial sensors; and
wherein the control device is configured to reduce the bending resistance of the knee joint based upon the angular velocity of the lower leg component not being zero.

14. The artificial orthotic or prosthetic device of claim 12 wherein the control device is configured to determine that the absolute angle of the lower leg component has reached the threshold value using information provided to the control device during the gait cycle by only the one or more inertial sensors positioned distal to the knee joint.

15. The artificial orthotic or prosthetic device of claim 12 wherein the one or more inertial sensors include at least one of a two dimensional magnetic field sensor, a three dimensional magnetic field sensor, a two dimensional acceleration sensor, a three dimensional acceleration sensor, a one dimensional gyroscope, a two dimensional gyroscope, and a three dimensional gyroscope.

16. The artificial orthotic or prosthetic device of claim 12 wherein the control device is configured to determine that the absolute angle of the lower leg component has reached the threshold value using information provided to the control device during the gait cycle by at least two of the inertial sensors.

17. The artificial orthotic or prosthetic device of claim 12 wherein the threshold value is a value of the absolute angle of the lower leg component at an end of a standing phase of a patient.

18. The artificial orthotic or prosthetic device of claim 12 wherein the control device is configured to modify the bending resistance of the knee joint using the resistance device based upon the absolute angle of the lower leg component reaching the threshold value by switching the bending resistance to one of two fixed values.

19. The artificial orthotic or prosthetic device of claim 12
wherein the control device is configured to determine, using information provided to the control device during the gait cycle by the one or more inertial sensors, that an angular velocity of the lower leg component has reached zero signifying a reversal of a movement direction of the lower leg component; and
wherein the control device is configured to modify the bending resistance of the knee joint using the resistance device based upon the angular velocity of the lower leg component reaching zero signifying the reversal of the movement direction of the lower leg component.

20. The artificial orthotic or prosthetic device of claim 12
wherein the control device is configured to determine that an angular acceleration of the lower leg component has exceeded a threshold acceleration value using information provided to the control device during the gait cycle by the one or more inertial sensors; and
wherein the control device is configured to maintain or increase the bending resistance of the knee joint based upon the angular acceleration of the lower leg component exceeding the threshold acceleration value.

21. The artificial orthotic or prosthetic device of claim 12 wherein the control device is configured to determine that the absolute angle of the lower leg component has reached the threshold value using electronic signals provided to the control device during the gait cycle by only the one or more inertial sensors.

\* \* \* \* \*